(12) United States Patent
Lönne et al.

(10) Patent No.: US 8,038,801 B2
(45) Date of Patent: Oct. 18, 2011

(54) METHOD AND APPARATUS FOR THE CLEANING OF COMPONENTS OF A POWER PLANT BY THE INJECTION OF A MEDIUM AND MEASURING DEVICE FOR MEASURING THE DEGREE OF PURITY OF THE MEDIUM

(75) Inventors: Rolf Lönne, Hallerndorf (DE); Jan Elsen, Hemhofen (DE); Robert Karl, Mainz (DE)

(73) Assignee: Siemens Aktiengesellschaft, Munich (DE)

( * ) Notice: Subject to any disclaimer, the term of this patent is extended or adjusted under 35 U.S.C. 154(b) by 305 days.

(21) Appl. No.: 12/086,403

(22) PCT Filed: Oct. 26, 2006

(86) PCT No.: PCT/EP2006/067791
§ 371 (c)(1),
(2), (4) Date: Jun. 12, 2008

(87) PCT Pub. No.: WO2007/071478
PCT Pub. Date: Jun. 28, 2007

(65) Prior Publication Data
US 2009/0107532 A1    Apr. 30, 2009

(30) Foreign Application Priority Data

Dec. 16, 2005 (EP) .................................. 05027687

(51) Int. Cl.
*B08B 7/04* (2006.01)
*B08B 9/093* (2006.01)

(52) U.S. Cl. ........... 134/18; 134/10; 134/11; 134/22.18; 134/56 R; 134/108; 134/113; 134/166 R

(58) Field of Classification Search .................... 134/10, 134/11, 18, 22.1, 22.11, 22.12, 22.18, 34, 134/56 R, 57 R, 58 R, 105, 106, 107, 108, 134/113, 166 R, 166 C, 37
See application file for complete search history.

(56) References Cited

U.S. PATENT DOCUMENTS

| | | | | |
|---|---|---|---|---|
| 1,495,964 | A | * | 5/1924 | Reid .................... 137/630.18 |
| 2,832,673 | A | * | 4/1958 | Larson et al. .................... 436/38 |
| 3,158,444 | A | * | 11/1964 | Larson et al. .................... 436/38 |
| 3,199,494 | A | * | 8/1965 | Strohmeyer, Jr. ............. 122/1 B |
| 3,538,930 | A | * | 11/1970 | Kowalski .................... 137/81.2 |
| 4,251,220 | A | * | 2/1981 | Larson et al. ................ 436/103 |
| 4,387,592 | A | * | 6/1983 | Welker ............................ 73/198 |
| 4,841,787 | A | * | 6/1989 | Waterman .................... 73/866.5 |
| 4,921,546 | A |   | 5/1990 | Bloch |
| 5,159,955 | A | * | 11/1992 | Ekman .................... 137/614.03 |
| 5,840,130 | A |   | 11/1998 | Liebig et al. |
| 6,158,717 | A | * | 12/2000 | Van Scyoc et al. ......... 251/149.6 |
| 6,594,017 | B1 |   | 7/2003 | Menden |
| 2004/0013511 | A1 | * | 1/2004 | Brackenhammer et al. ...... 415/1 |
| 2005/0001634 | A1 | * | 1/2005 | Kaiser et al. .................. 324/658 |
| 2006/0053791 | A1 | * | 3/2006 | Prentice, III .................... 60/645 |
| 2006/0097215 | A1 | * | 5/2006 | Pohn et al. .................... 251/327 |

FOREIGN PATENT DOCUMENTS

| | | |
|---|---|---|
| DE | 91 04 279 U1 | 7/1991 |
| EP | 0 776 707 A2 | 6/1997 |
| WO | WO 2004003413 A1 * | 1/2004 |

* cited by examiner

*Primary Examiner* — Alexander Markoff

(57) ABSTRACT

The invention relates to a method for cleaning plant components of a power station, wherein a medium is continuously passed through one or more plant components for cleaning a closed circuit and a check of the medium for degree of purity is carried out in at least one operating plant component.

12 Claims, 7 Drawing Sheets

FIG 4
FIG 5
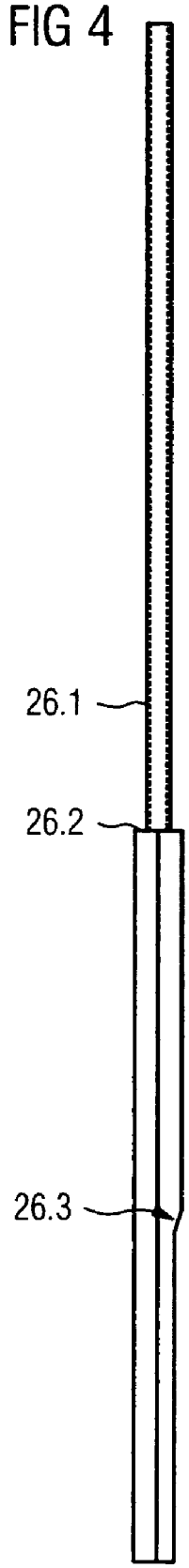
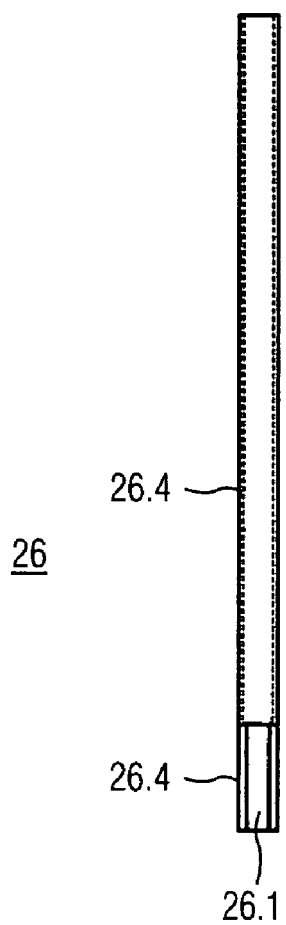
26

METHOD AND APPARATUS FOR THE CLEANING OF COMPONENTS OF A POWER PLANT BY THE INJECTION OF A MEDIUM AND MEASURING DEVICE FOR MEASURING THE DEGREE OF PURITY OF THE MEDIUM

CROSS REFERENCE TO RELATED APPLICATIONS

This application is the US National Stage of International Application No. PCT/EP2006/067791, filed Oct. 26, 2006 and claims the benefit thereof. The International Application claims the benefits of European application No. 05027687.2 filed Dec. 16, 2005, both of the applications are incorporated by reference herein in their entirety.

FIELD OF INVENTION

The invention relates to a method for the cleaning of components of a power plant, in particular of a steam turbine plant or of a gas and steam turbine plant. It relates, furthermore, to an apparatus for the cleaning of components of a power plant, into which apparatus a medium, in particular a vaporous medium, is introduced, in particular injected. It relates, further, to a measuring device for measuring the degree of purity of the medium and for use in the apparatus for cleaning the components.

BACKGROUND OF THE INVENTION

The purity of the steam in the operation a power plant has to satisfy stringent requirements. In particular, it is important to avoid the situation where particulate solids are entrained in the steam. Such solid particles may lead to damage to the plant parts, such as, for example, the turbine. Damage in this case occurs particularly on the blading and the labyrinth seals of the turbine.

To protect the turbine and other plant parts against relatively large solid particles, steam screens are installed upstream of quick-closing interception valves or between quick-closing interception valves and the regulating valves in the steam lines. By contrast, solid particles of smaller diameter pass through the screens. They can therefore enter the turbine. These cause what is known as solid state erosion of the blading. This leads to material stripping and blade toughening and consequently to the impairment of turbine efficiency. In so far as the solid particles are braked by the turbine and they remain in the turbine, there is the risk that they lead to rougheings on the blading and possibly form deposits in the labyrinth seals.

These deposits may damage or destroy sealing elements or other components.

In boilers, steam lines or other steam-carrying components which lie upstream of the turbine in the steam flow direction, solid particles arise, in particular during the new installation of power stations. Solid particles occur even during plant inspections or component exchange. These solid particles are, in particular, rolling skin, scale, iron oxides and corrosion products and oxidation layers caused by the heat treatment of the plant components. Even with the greatest care during installation work, the situation cannot be certainly be avoided where dust, sand, installation objects and installation waste are left behind in steam-carrying components or plant parts of the plant. The impurities are sometimes present loosely. Sometimes, they adhere to the inner walls of the plant parts.

In general, therefore, as steam-carrying components, the boiler region, steam lines between the boiler and steam turbine or between the boiler and condenser, and also valves, have to be blown out or flushed out before every first steam pulse of a steam turbine and thereby freed of particles, in particular of solid particles, for example rolling skin, scale or iron oxides.

A scavenging method is employed for cleaning the power plant. After the scavenging or pickling of the plant has taken place, the steam-carrying systems are cleaned by means of steam. This is generated by the evaporation of water of highest purity (demineralized water) in the boiler. In this case, the water of highest purity is supplied to the power plant, led through the corresponding components and extracted again. Thus, for example, before every first steam pulse of a steam turbine, the steam-carrying boiler regions and the steamlines are freed of particles which may lead to damage and/or to an impairment of efficiency. This cleaning process is subject to various parameters, such as, for example, demineralized water generation capacity, demineralized water storage capacity and rapid demineralized water afterfeed, sound protection measures, resulting operational restrictions, evidence of freedom of the steam from particles, removal of temporary facilities, subsequent dependent commissioning steps.

In the cleaning of the current parts, temporary cleaning facilities connectable to the power plant are provided, which supply the scavenging medium to the power plant and extract again at least part of the scavenging medium after it has flowed through the components.

In conventional methods, the cleaning of the steam-carrying plant parts takes place by means of chemical cleaning (such as, for example, pickling) or by burning out with steam or by a combination of the methods.

In pickling, the cleaning waters are laden with a pickling agent, for example inhibited acid, complex formers, for example ethylene-diamine-tetraacetic acid, and therefore cannot be discharged into the environment. Considerable outlays are required for the disposal of the waste water laden with chemicals.

Superheaters, reheaters and associated steamlines are usually blown out with steam. In this case, it is appropriate to adhere to conditions which ensure that solid particles which have remained in the plant parts despite the blowing out with steam are not entrained by the operational steam flow during the operation of the plant.

Blowing out is therefore effective only at higher flow velocities than are to be expected when the plant is operating under full loading. According to experience, the dynamic pressure in blowing out amounts to 1.2 to 1.7 times the value of the dynamic pressure during operation at the maximum continuous output of the plant.

This blow-out condition can be fulfilled both in the case of continuous blowing out at relatively low pressure and in the case of discontinuous blowing out at relatively high pressure.

Both methods—pulse-like or continuous steam blow-out—are based on the fact that the steam discharged into the atmosphere has to be replaced by the afterfeed of fully deionized water (=demineralized water). The steam cleaning duration is therefore always dependent on the demineralized water generation capacity or demineralized water storage capacity. Furthermore, complicated blow-out facilities are necessary in order to ensure a rapid afterfeed of demineralized water into the condensate system and in order to limit the sound emissions occurring during atmospheric steam blow-out to the required sound levels. For example, for this purpose, silencers are used, or water injection into the steam takes place and therefore leads to an additional water demand. Also, the conventional circulatory cleanings cannot be carried out uninterruptedly, since the assessment of the freedom of the steam from particles is not possible online in high temperature and pressure ranges.

SUMMARY OF INVENTION

The object on which the invention is based, therefore, is to specify a method, improved in relation to the prior art, for the cleaning of plant parts of a power plant. Furthermore, a particularly simple apparatus for the cleaning of plant parts and a particularly suitable measuring device are to be specified.

The first mentioned object is achieved, according to the invention, by means of the subject of the claims. In terms of the apparatus, the object is achieved by means of the features of the claims. In terms of the measuring device, the object is achieved by means of the features of the claims.

Advantageous developments of the invention are the subject matter of the sub claims.

The invention in this case proceeds from the consideration that, for as uninterrupted a cleaning process as possible for, in particular, steam-carrying plant parts of a power plant, the cleaning process should be carried out in circulatory operation. In this case, as medium, steam condensed in the condenser is routed continuously in a closed flow circuit through one or more plant parts to be cleaned, a testing of the medium for its degree of purity being carried out in at least one operational plant part. It thereby becomes possible to clean without interruption until the required freedom from particles is achieved, with the result that, in turn, the cleaning times are reduced considerably. Whether the required freedom from particles is present is detected by means of a measuring device arranged directly in an operational plant part. By means of closed steam cleaning the cleaning process is independent of the demineralized water generation capacity or demineralized water storage capacity. There is also no need for a rapid afterfeed of the demineralized water, since the closed cleaning process can be carried out virtually without any water loss.

Preferably, the degree of purity of the medium, in particular of the steam, is tested in an operational and therefore permanent steam line. As a result, required steam cleaning parameters and cleaning steps can be tested, during cleaning, in the operational plant part itself and can therefore be set without interruption. Additionally or alternatively, the degree of purity of the medium can be tested in a temporary line. A temporary line is understood as meaning, in particular, a temporary steam line, required and to be installed for the cleaning process, for bypassing the high-pressure steam turbine.

In one possible embodiment for a circulatory operation of the cleaning process, the degree of purity of the medium is tested when the power plant is in condensation operation.

On account of the low sound level load in condensation operation, the cleaning process is independent of daytime, weekend or holiday restrictions and can be carried out while the power plant is operating continuously.

To clean the plant parts by means of steam in circulatory operation, in this case, steam is extracted from a steam boiler device, and liquid obtained from the steam in a condenser is supplied to the operational plant part or plant parts and routed in a closed flow circuit. In the case of a plant comprising a steam turbine unit, this is bypassed by the flow circuit and is not acted upon by steam during cleaning. The sensitive parts of the steam turbine are therefore not damaged by foreign bodies or particles blown out. However, the steam turbine is rotated hydraulically during condensation operation, in order to avoid a shaft distortion which would be caused by the heat radiation of the steam in the steam space of the condenser. In condensation operation, therefore, the steam turbine is in what is known as rotary operation, and the condenser is evacuated on the steam side and cooled by cooling water on the cooling water side.

Preferably, as plant parts to be cleaned, at least one boiler or, in series or in parallel, a plurality of boilers are included in the steam circuit, and subsequently, in steps, further operational plant parts which in the power plant follow the already cleaned plant parts in flow terms are connected into the closed flow circuit.

In other words; the closed cleaning process allows a parallel system commissioning of a gas turbine, boiler and water/steam circuit and of bypass stations up to the base load of the plant. The time point for the removal of required temporary blow-out facilities can thus be predetermined and planned. On account of the cleaning, which has taken place in normal condenser operation, in a closed circuit, particularly simple blow-out facilities reduced to only a few components become possible. Moreover, the reduced extent of blow-out facilities shortens the removal time required for restoring the plant state after each cleaning. In the present method, the blow-out facilities provided are merely a temporary steam line system for bypassing the high-pressure stage of the steam turbine.

The apparatus comprises, for the cleaning of plant parts of a power plant in a closed flow circuit, at least one measuring device, connectable to an operational plant part, for measuring the degree of purity of the medium (also designated as a "baffle plate changing device"). The measuring device in this case comprises, for testing the steam purity, a measuring apparatus which can be introduced directly into an operational steam line and which is designed to be correspondingly pressure-resistant and temperature-resistant. In particular, the measuring apparatus is designed to be sufficiently resistant with respect to a pressure of approximately 40 bar and a temperature of 550° C.

By virtue of the design of the measuring apparatus in terms of a predetermined pressure resistance, the measuring device is suitable for connection to a medium-pressure or low-pressure steam line (also referred to briefly below as "medium-pressure, reheater or low-pressure steam line"). As a result, the measuring device can be connected in a flanged version to a connection piece of one of the permanent or operational steam lines, in particular to the low-pressure steam line and/or to a medium-pressure steam line. It is also possible to connect the measuring device to a connection of a temporary line, for example to the connection piece of the temporary steam line for bypassing the high-pressure steam turbine.

For monitoring and testing the steam purity, the measuring device connected to one of the steam lines is opened, in particular temporarily opened, when the power plant is in condensation operation.

For a pressure-resistant and temperature-resistant design of the measuring device, the latter comprises of at least one flanged connection for connecting to a connection piece of the operational steam line and a double shut-off designed as a lock fitting. The double shut-off allows separation between the steam space of the steam line and the lock space and serves for the reliable shut-off after the lock operation and pressure relief. For pressure relief, the double shut-off expediently has between the two shut-off fittings a shut-off valve designed as a relief valve. The pressure relief between the two shut-off fittings of the double shut-off may serve at the same time as a leakage check during the first shut-off of the two shut-off fittings. If required, a cooling element may additionally be connected to the double shut-off.

The flanged connection is designed, for example, as a standard 3" flanged connection (=3-inch flanged connection). Such dimensioning serves for the reliable reception of a lower bearing in the connection piece for the measuring apparatus which can be introduced into the operational plant part in order to test the degree of purity of the steam.

In a preferred embodiment, the double shut-off is provided on the inlet side and/or on the outlet side with at least one elastic sealing element. The sealing elements are designed elastically in such a way that temperature gradients are compensated.

The flanged connection below the lock comprises a support bearing in the region of the connection piece to the steam space. This support bearing serves for receiving the measuring apparatus which is fastened to a spindle end. As a result, the locking of the measuring apparatus into the steam line and therefore into a vibrating flow presents no problems and does not have to be limited in time.

The support bearing is preferably designed as a sleeve with a peripheral margin or a cone. For this purpose, the support bearing has at least partially a chamfered inner step, in particular with an angle greater than 18°. The chamfered or oblique inner step serves for simple reception and mounting. The measuring apparatus, which is likewise designed to be chamfered correspondingly to the chamfer angle of the inner step in the region of the fastening, is thereby mounted particularly securely.

In order to prevent loose parts, for example fastening screws, from falling into the steam space, the fastening of the measuring apparatus is designed to be encapsulated in the locked-in state. Furthermore, by means of the fastening, the depth of penetration of the measuring apparatus into the steam line can be set. To lead the measuring apparatus into and out of the steam line, a mechanical drive, in particular a threaded spindle with a nut, is provided. The threaded spindle, which can be actuated mechanically via a motor or manually via a handwheel, is designed to be expansion-compensated and temperature-compensated and is surrounded by a housing. The spindle end leads as a rotary spindle out of the housing where the drive is fastened. The arrangement of the spindle nut and the compensation of the latter against expansions and displacements prevent an otherwise usual sluggishness due to the introduction of dirt or to high temperatures.

When the measuring apparatus is being led in and out and therefore being changed, the housing located above the double shut-off or lock fitting is pressure-relieved in a directed manner before opening in order to extract the measuring apparatus. The opening of the housing subsequently takes place via a further flanged connection provided in the region above the double shut-off. The flanged connection is provided with a seal which allows easy opening and closing. A further relief valve for the pressure relief of the housing is provided both below the flanged connection and in the upper housing part.

Furthermore, relief and cooling can take place in a directed manner, and the leaktightness of the double shut-off can be monitored.

For a simple arrangement of the measuring device on the steam line, a mounting is provided which is designed, in particular, as a saddle mounting on the steam line itself. A rigid connection to the tubular steam line is consequently produced, so that relative movements are avoided. This makes it possible to have a sufficiently reliable fastening, even for continuous use of the measuring device on the steam line.

The advantages achieved by means of the invention are, in particular, that, by steam cleaning in circulatory operation during the condensation of the steam in the condenser and therefore when the plant is condensation operation, a testing of the degree of purity of the steam in the operational steam line becomes possible, and cleaning can be carried out virtually without any water loss. The cleaning process is thus made possible virtually independently of the demineralized water generation capacity, storage capacity and afterfeed. Due to cleaning in circulatory operation, complicated sound protection measures may be dispensed with because of the extremely low-noise process. Moreover, merely simple and only few blow-out facilities are required, and therefore the removal time necessary for restoring the normal operational plant state is markedly reduced.

BRIEF DESCRIPTION OF THE DRAWINGS

An exemplary embodiment of the invention is explained in more detail with reference to a drawing in which:

FIG. 3 to 9 show components of the measuring device in a detailed illustration.

Identical parts are given the same reference symbols in all the figures.

DETAILED DESCRIPTION OF INVENTION

Figure 1:
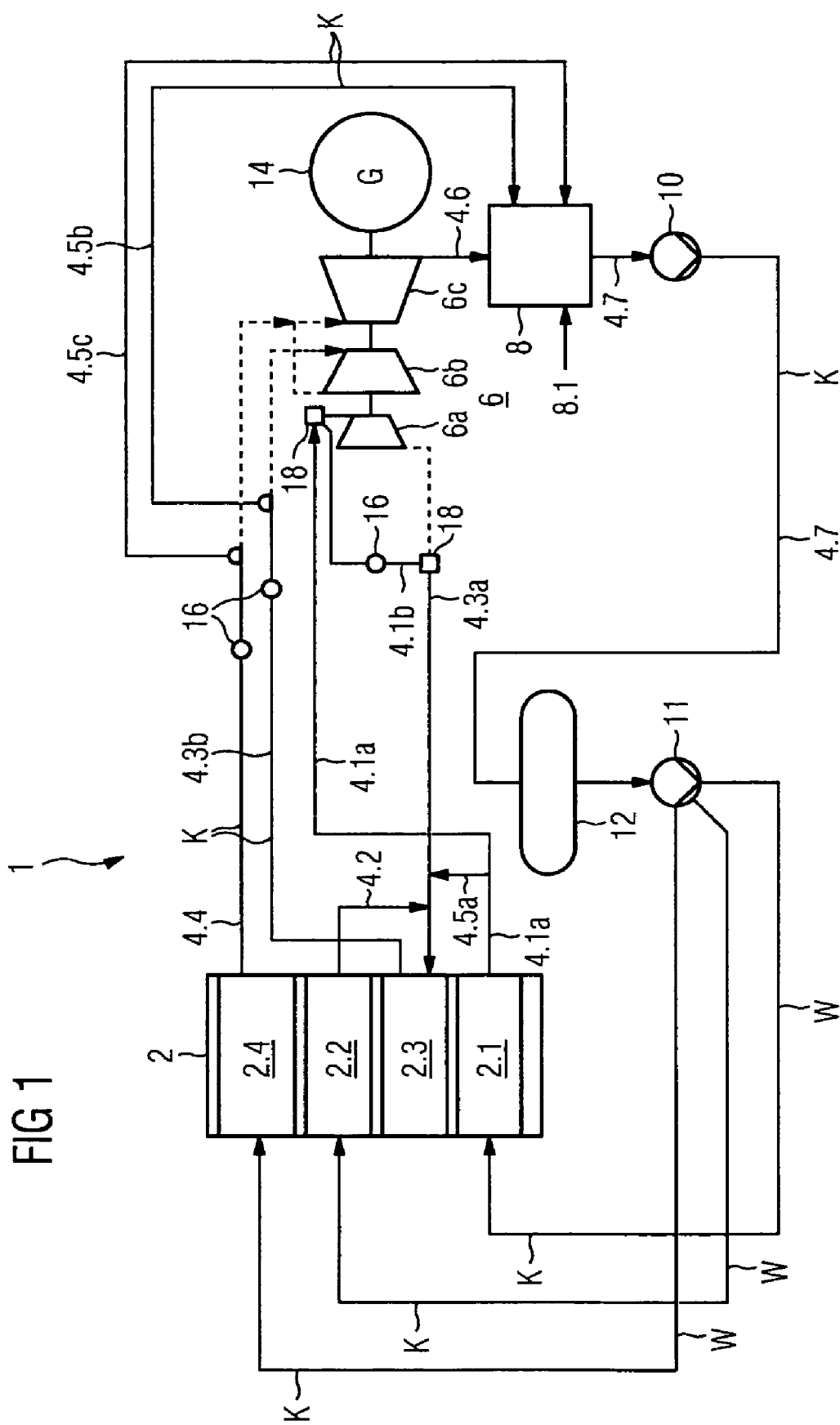
FIG. 1 shows a rough diagrammatic illustration of the plant parts of a power plant which are provided for the cleaning process, with a steam boiler device and with a steam turbine device, and also the measuring device provided for the method according to the invention and the blow-out facilities provided.

FIG. 1 shows a closed flow circuit K for cleaning the plant parts of a power plant 1. The closed flow circuit K is identified by a double line.

The power plant 1 comprises a steam boiler device 2 with a plurality of pressure stages 2.1 to 2.4, for example consisting of a high-pressure part, of a medium-pressure part, of a low-pressure part and of a reheater, which feed a steam turbine unit 6 via steam lines 4.1a, 4.3b and 4.4 when the power plant 1 is in normal operation. The components of the power plant 1 which are bypassed in the cleaning process are identified by a dashed line.

In normal operation, a steam line 4.6 goes from the steam turbine unit 6 to a recirculation device which comprises a condenser 8 and a condensate pump 10, in order to supply the water obtained from the condensed steam to the steam boiler device 2 again via a return line 4.7. Water losses are compensated via the supply line 8.1 and are added to the feed water tank 12 via the condenser 8 and the return line 4.7. For the afterfeed of the steam boiler device 2, the water is available, stored in the feed water tank 12. When the power plant 1 is in normal operation, a generator 14 for generating electrical current is driven by means of the steam turbine unit 6.

To free the steam-carrying plant parts of the steam boiler device 2.1 to 2.4, 4.1a, 4.2, 4.3a, 4.3b, 4.4 and the operational bypass lines 4.5a, 4.5b and 4.5c of particles, steam as scavenging medium flows through them, bypassing the steam turbine unit 6, in the closed flow circuit K. The bypassed steam turbine unit 6 and other bypassed components, such as the generator 14, are illustrated by dashes. To bypass the steam turbine unit 6, in each case a steam bypass line 4.5b and 4.5c issuing into the condenser 8 emanates from the steam lines 4.3b and 4.4.

The steam line 4.6 bypassed in condensation operation, that is to say the low-pressure turbine exhaust steam line, to the condenser 8 is acted upon with steam only after steam cleaning has taken place, that is to say when the steam turbine unit 6 is pulsed with steam. The return line 4.7 is a condensate line which is already cleaned during scavenging in the preceding cleaning process.

The cleaning of the steam-carrying plant parts 2.1 to 2.4 of the steam boiler device 2 and of the steam lines 4.1a, 4.2, 4.3a, 4.3b, 4.4, 4.5a to 4.5c takes place while the plant 1 is in condensation operation. In this case, the scavenging medium used on the waterside is purified and deionized water, in particular demineralized water, which is supplied via the supply line 8.1 to the condensate system 4.7 and, if appropriate, is available, stored in the feed water tank 12. Steam is generated from this scavenging medium in the boiler pressure stages 2.1, 2.2 and 2.4. To monitor the degree of purity of the steam, a measuring device 16 for measuring the degree of purity of the medium (referred to briefly below as the "measuring device 16") is provided on at least one of the plant parts 4.1b, 4.3b and 4.4. The measuring device 16 is designed as a baffle plate change device.

The measuring device 16 is designed to be appropriately pressure-resistant and temperature-resistant particularly for installation in the temporary steam line 4.1b and for the operational steam lines 4.3b, 4.4, in particular a medium-pressure or low-pressure steam line.

In a power plant 1 having a high-pressure stage, to bypass the high-pressure stage of the steam turbine unit 6, a branch from the high-pressure steam line 4.1a is provided for temporary cleaning facilities with a temporary steam line system 4.1b and blow-out inserts 18 and with a measuring device 16 arranged between the blow-out inserts 18.

When the steam-carrying components of the boiler pressure stages 2.1 to 2.4 and the steam lines 4.1a, 4.2, 4.3a, 4.3b, 4.4, 4.5a to 4.5c of the power plant 1 are being blown out by means of steam, in particular steam of highest purity, only the steam routed in the temporary steam line system 4.1b for bypassing the high-pressure stage of the steam turbine unit 6 is blow out via the blow-out inserts 18.

When the power plant 1 is in normal operation, the high-pressure stream line 4.1a issues into the high-pressure stage 6a of the steam turbine unit 6.

The closed flow circuit K for cleaning the plant parts 4.1a, 4.2, 4.3a, 4.3b, 4.4, 4.5a to 4.5c and the steam boiler device 2 with the individual pressure stages 2.1 to 2.4 is described in more detail below. The cleaning of the plant parts 4.1a, 4.2, 4.3a, 4.3b, 4.4, 4.5a to 4.5c and of the steam boiler device 2 with the individual steam-carrying pressure stages 2.1 to 2.4 may take place in each case in succession. That is to say, first, the high-pressure and the medium-pressure part of the steam boiler device 2 are cleaned. For this purpose, the steam is routed out of the high-pressure stage of the steam boiler device 2 via the temporary steam line system 4.1b.

When the plant parts of the high-pressure stage are being blown through, the particles entrained by the steam are discharged via the blow-out inserts 18 in the temporary steam line system 4.1b, via the reheater 2.3 and via the medium-pressure bypass station in the medium-pressure bypass 4.5b.

In this case, steam also already flows through the reheater 2.3 and the low-pressure superheater of the boiler pressure stage 2.4, but the required steam parameters for cleaning these regions are not yet reached. In the steam cleaning of the reheater 2.3 and of the low-pressure superheater of the boiler pressure stage 2.4, the steam is routed via the operational high-pressure bypass line 4.5a; the temporary steam line system 4.1b is either already removed or bypassed and therefore does not have a through flow. In this step, the gas turbine output is raised to an extent such that the cleaning parameters for the reheater 2.3 and the low-pressure super heater of the boiler pressure stage 2.4 are reached.

The quality of the steam in terms of its freedom from particles or from foreign bodies is detected by means of the measuring device 16 at an appropriate location directly in one of the operational plant parts 4.3b and 4.4 or, in the case of high-pressure system cleaning, in the temporary steam line system 4.1b and is monitored during the cleaning operation.

Instead of one steam boiler 2, the steam turbine 6 may also be fed by a plurality of steam boilers 2 and 3. In this case, it is possible that the steam boilers 2 and 3, which are connected in parallel during normal operation, can also be connected in parallel in the scavenging medium circuit and therefore can be cleaned simultaneously. The overall cleaning duration can thereby be further reduced.

The measuring device 16 is described in more detail below with reference to FIG. 2 to 9.

Figure 2:
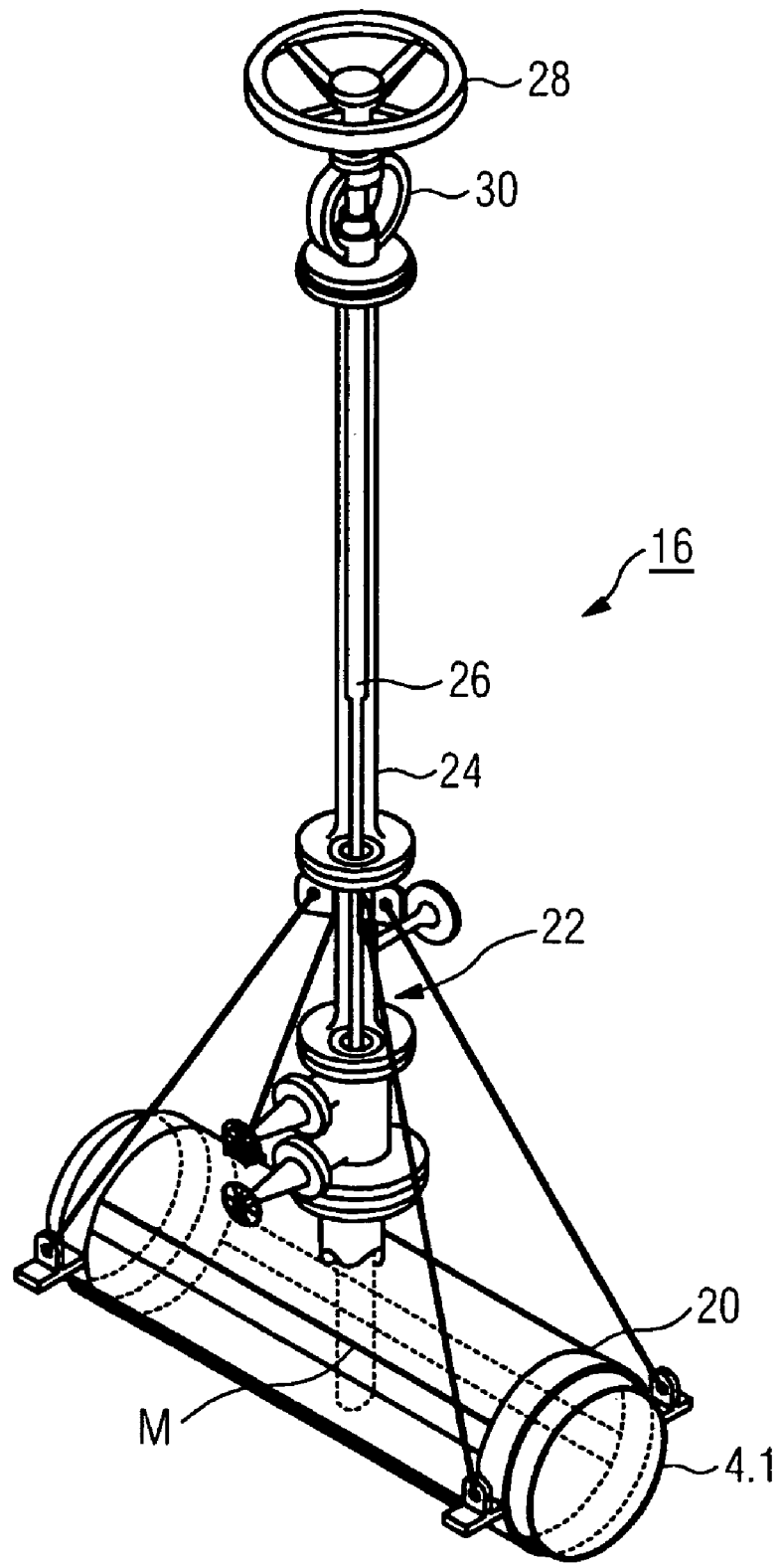
FIG. 2 shows a detailed illustration of a measuring device, connected to a plant part, for measuring the degree of purity of the medium.

FIG. 2 shows a measuring device 16 connected, for example, to a steam line 4.1, for example the high-pressure steam line 4.1a or the temporary steam line system 4.1b. Via a mounting 20 designed as a saddle mounting, the measuring device 16 is fastened rigidly to the tubular steam line 4.1, so that relative movements are avoided.

By means of the measuring device 16, what is known as a blow-out level (also called a "baffle plate") is introduced as a measuring apparatus M inside the steam line 4.1 during continuous operation. This is a polished metal strip, for example an aluminum, copper or steel strip. The measuring apparatus M is in this case introduced into the steam line 4.1 transversely with respect to the flow direction. The degree of purity of the medium is observed visually and judged, during the blow-out operation, by means of particle impacts impinging onto the measuring apparatus M.

The measuring apparatus M is designed as a baffle plate change device, so that it can be changed during operation, that is to say during blow-out, and during cleaning in continuous condensation operation.

In order to make exchange possible during blow-out, a double shut-off 22 is provided, which is designed as a locking fitting. Above the double shut-off 22 is arranged a tubular housing 24 with a threaded spindle 26. The threaded spindle 26 serves for leading the measuring apparatus M into and out of the steam space of the steam line 4.1. Leading in and out may take place manually via a handwheel 28 provided above the housing 24 or via a motor operated drive, not illustrated in any more detail. A drive 30 with a gland and its central cup spring pressure may also be provided.

Figure 3:
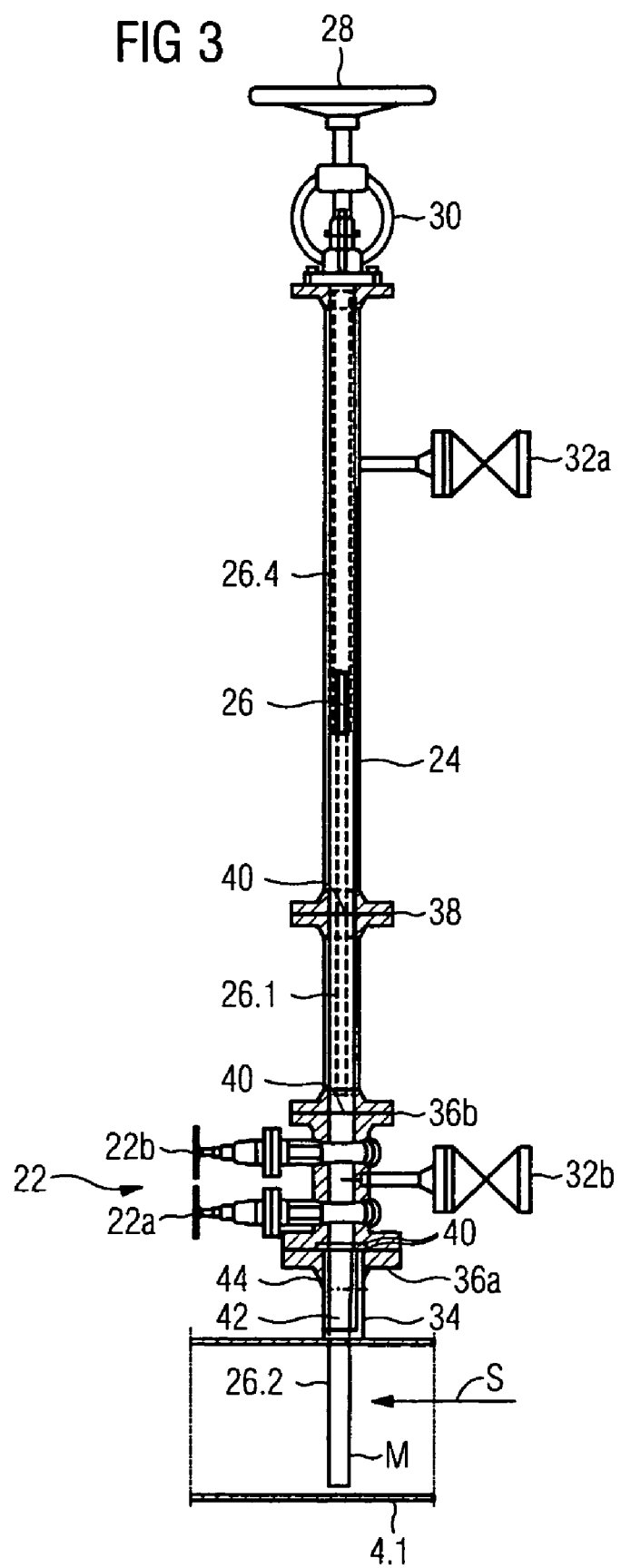

The housing 24 can be pressure-relieved in a directed manner. For this purpose, the measuring device 16 comprises two relief valves 32a, 32b, for example shut-off valves, which are illustrated in more detail in FIG. 3. FIG. 3 shows the measuring device 16 in detail.

One of the shut-off valves 32a is arranged above the double shut-off 22 on the housing 24 for the pressure relief of the housing 24. The other shut-off valve 32b is arranged between the shut-off fittings 22a, 22b of the double shut-off 22 for the pressure relief of the lock space. For this purpose, the double shut-off 22 is designed as a unit or as a block fitting consisting of two shut-off fittings 22a, 22b in the form of a rotary table. The pressure relief brought about by means of the respective relief valve 32b between the two shut-off fittings 22a, 22b serves at the same time as a leakage check for the first shut-off 22a.

The measuring device 16 is connected to a connection piece 34 of the steam line 4.1 via a flanged connection 36a of the double shut-off 22. A further flanged connection 36b for connecting the housing 24, if appropriate via an intermediate flange 38, is provided at the other end of the double shut-off 22.

Elastic sealing elements 40 are provided on the inlet side and the outlet side of the double shut-off 22 in the region of the flanged connections 36a, 36b and, if appropriate in the region of the intermediate flange 38, in order to absorb temperature gradients.

The flanged connection 36a on the connection piece 34 is designed as a 3" flanged connection. This dimensioning makes it possible to form a lower bearing 42 in the connection piece 34. The lower bearing 42 comprises a support bearing 44 which is installed in the connection piece 34 to the steam space and which is arranged below the lock fitting 22. The lower bearing 42 receives the spindle end of the threaded spindle 26, to which spindle end is fastened the measuring apparatus M which can be introduced into the steam line 4.1 transversely with respect to the flow direction S.

FIG. 4 shows in detail the threaded spindle 26 which is formed from a threaded rod 26.1, for example with a trapezoidal external thread, and of a lower spindle housing 26.2 for receiving the measuring apparatus M. The lower spindle housing 26.2 is provided with an internal thread for guiding the threaded rod 26.1. The lower spindle housing 26.2 has an inwardly chamfered step 26.3, a space region for fastening the measuring apparatus M being formed above the step 26.3. Below the step 26.3, the spindle housing 26.2 serves for receiving the measuring apparatus M. FIG. 5 shows the upper spindle housing 26.4 which is provided as a threaded bush with a trapezoidal internal thread for leading the threaded rod 26.1 in and out.

Figure 6:
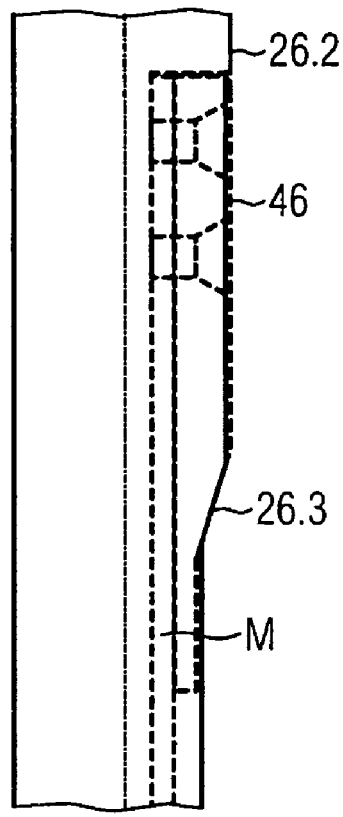
Figure 7:
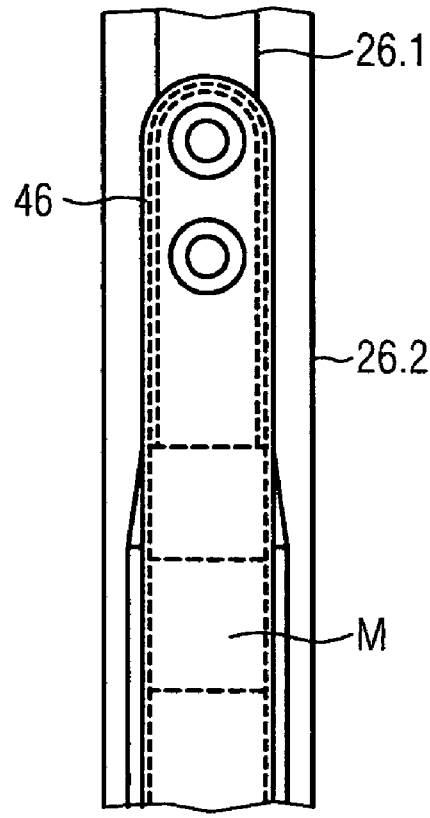

FIG. 6 and FIG. 7 show one possible embodiment of a fastening 46 of the measuring apparatus M on the threaded rod 26.1. The fastening 46 is designed as a double screw with chamfered step which is formed correspondingly to the step 26.3 of the lower spindle housing 26.2 and is received by the latter, in particular lies on the latter. The fastening 46 of the measuring apparatus M is thereby encapsulated in the locked-in state, and therefore no fastening screws or loose parts can fall into the steam space.

Figure 8:
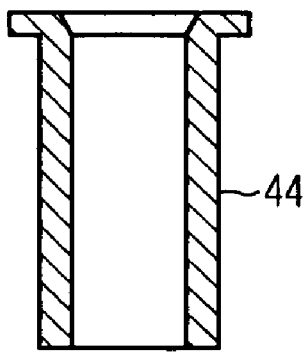
Figure 9:
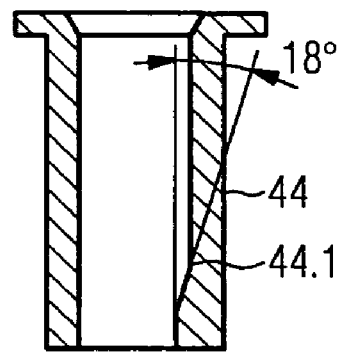

FIG. 8 and FIG. 9 show the support bearing 44 for receiving the spindle end, that is to say the lower spindle housing 26.2, in detail. For the reception, particularly the support, of the fastening 46 of the measuring apparatus M, the support bearing 44 has a step 44.1, in particular a chamfered step, for example with an angle of approximately 18°, said step corresponding to the step 26.3 of the spindle housing 26.2. The support bearing 44 is designed as a sleeve with a peripheral margin R which is held in the flanged connection 36a.

The method for exchanging the measuring apparatus M is described in detail below.

In the case of a threaded spindle 26 which, depending on the embodiment, is manual or is motor-driven, for example in the case of a manual drive, the handwheel 28 is rotated upward until it stops. The lower shut-off fitting 22a of the double shut-off 22 is subsequently closed. The relief valves 32a and 32b are opened until steam no longer arrives. For additional safety, the upper shut-off fitting 22b of the double shut-off 22 is closed.

After cooling, the upper row of screws of the intermediate flange 38 is opened, and the threaded spindle 26 together with the housing 24 is drawn upward and appropriately fastened for the exchange of the measuring apparatus M together with the measurement sample.

The handwheel 28 is rotated downward until the fastening 46 of the measuring apparatus M becomes visible. The measuring apparatus M can subsequently be exchanged after the release of the fastening 46. After a new measuring apparatus M has been attached, the handwheel 28 is rotated upward. The threaded spindle 26 is placed with the housing 24 onto the intermediate flange 38 again, an exact position being important for a good fit of the sealing element 40. The intermediate flange 38 is then closed. The relief valves 32, 32b are also closed. The double shut-off 22, that is to say the two shut-off fittings 22a, 22b, are opened, and the handwheel 28 is rotated downward until it stops, with the result that the measuring apparatus M is led into the steam line 4.1. In this case, the handwheel 28 is actuated by feel, that is to say is rotated into the cone until no vibration occurs.

Figure 10:
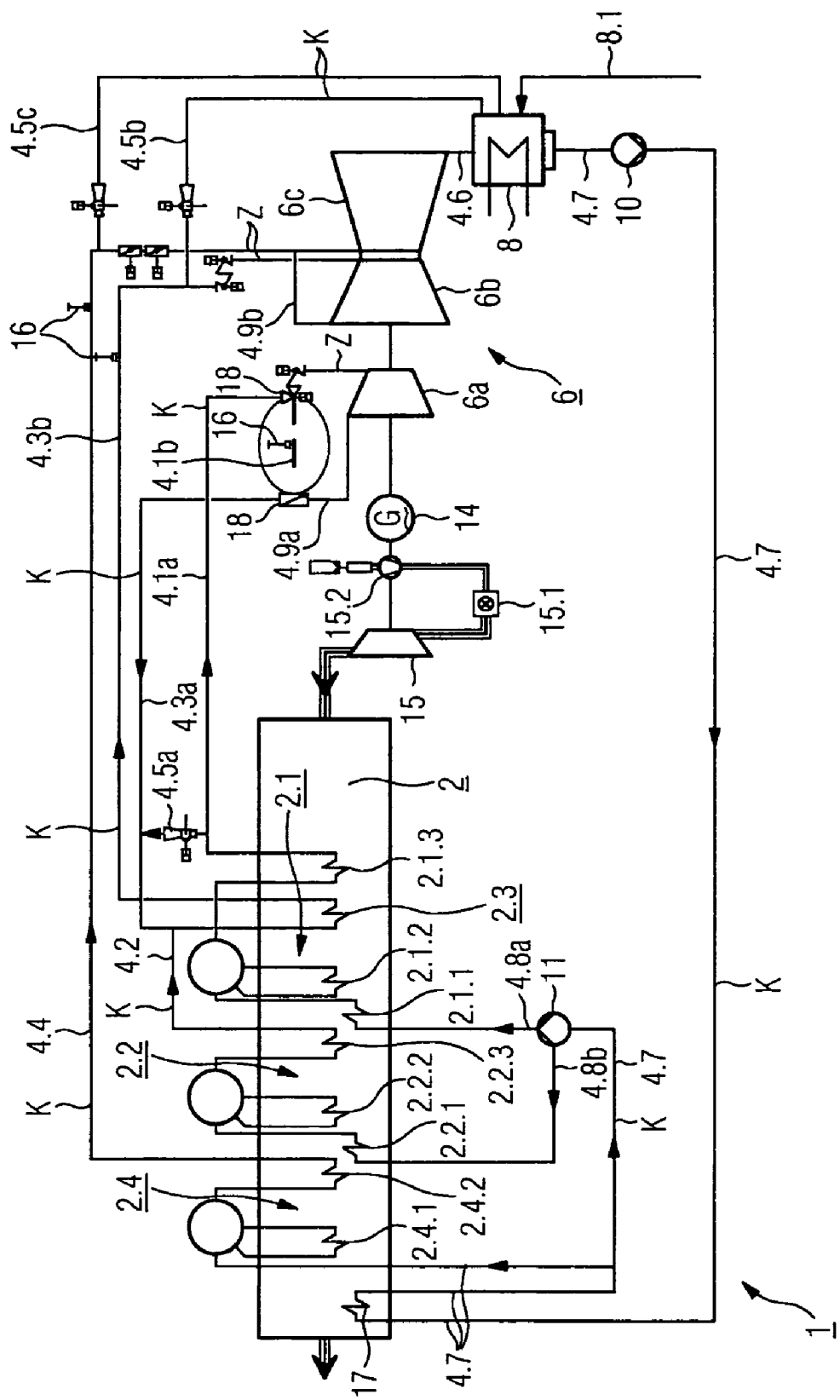
FIGS. 10 and 11 show a detailed illustration of a power plant with a plurality of plant parts to be blown through during the cleaning process.
Figure 11:
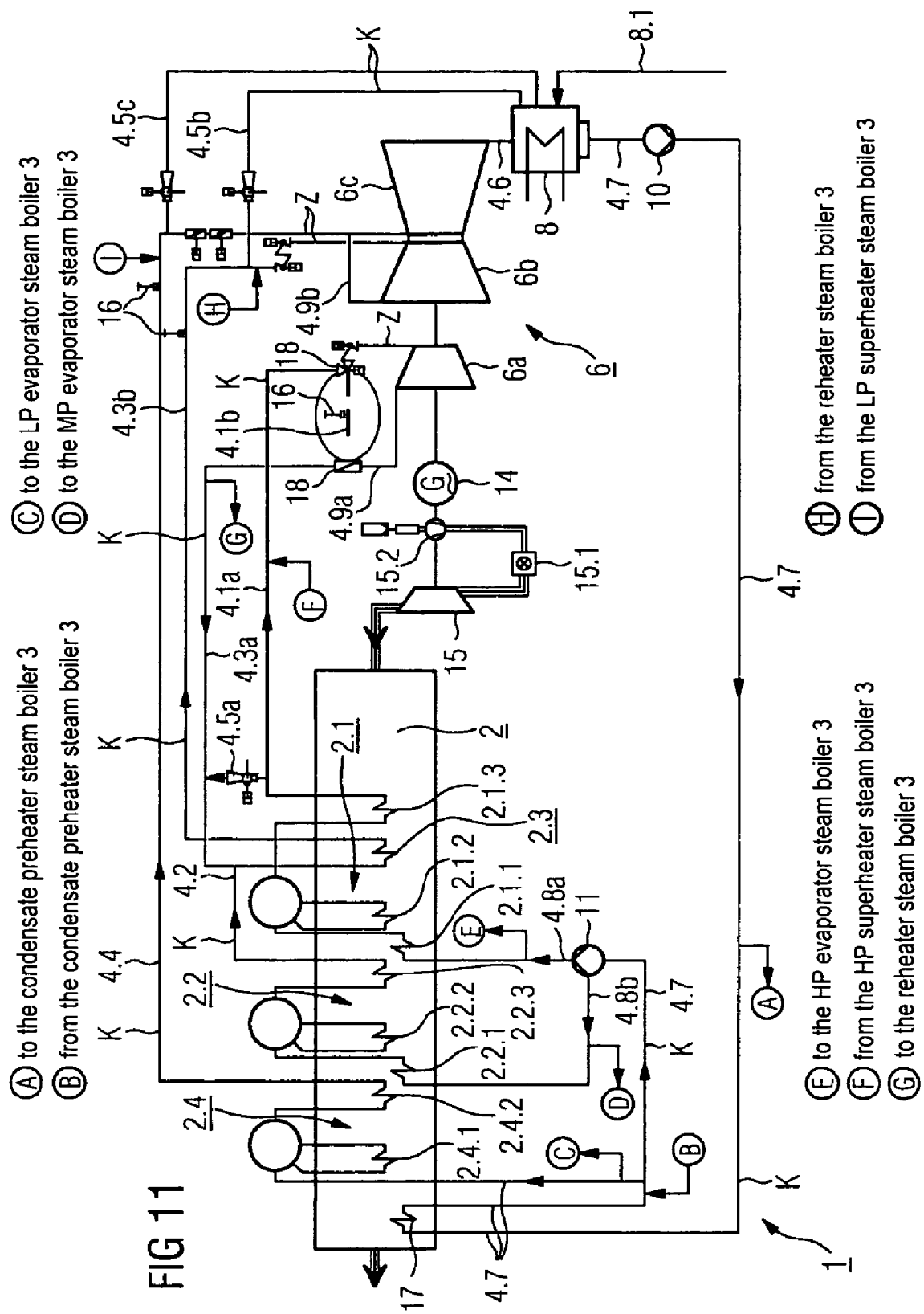

FIGS. 10 and 11 show two different exemplary embodiments of a closed flow circuit K for cleaning the steam-carrying plant parts of the boiler pressure stages 2.1 to 2.4 and the steam lines 4.1a, 4.2, 4.3a, 4.3b, 4.4, 4.5a to 4.5c of a power plant 1 with one or more steam boiler devices 2 or 2 and 3.

FIG. 10 shows, for example, a conventional gas and steam turbine plant with a 3-stage steam turbine unit 6, with a gas turbine 15 and with an individual steam boiler device 2 having a plurality of pressure stages with a high-pressure stage 2.1 consisting of a high-pressure economizer 2.1.1, of a high-pressure evaporator 2.1.2 and of a high-pressure super heater 2.1.3, with a medium-pressure stage 2.2 consisting of a medium-pressure economizer 2.2.1, of a medium-pressure evaporator 2.2.2 and of a medium-pressure super heater 2.2.3, with a reheater 2.3 and with a low-pressure stage 2.4 consisting of a low-pressure evaporator 2.4.1 and of a low-pressure super heater 2.4.2. The pressure stages 2.1 to 2.4 of the steam boiler device 2 are preceded by a condensate preheater 17.

FIG. 10 shows a high-pressure drum boiler. Instead of the high-pressure drum boiler, a forced-flow steam generator may also be installed. If appropriate, in addition to the feed water pump 11, a feed water tank or a degasser may be arranged in the condensate line 4.7. The power plant 1 is a single-shaft plant in which one generator is provided jointly for the gas turbine and the steam turbine. The same applies to FIG. 11.

FIG. 10 illustrates the closed flow circuit K for cleaning the operational plant parts 2.1.3, 4.1a, 2.2.3, 4.2, 4.3a, 4.3b, 2.4.2, 4.4, 4.5a to 4.5c of the power plant 1 by a double line. The components 4.6, 4.9a, 4.9b of the steam turbine units 6 which are illustrated by a thick solid line are in this case bypassed. The supply lines Z are closed by means of fittings, so that these and also the steam turbine unit 6 are likewise bypassed and steam does not flow through them; the steam turbine unit 6 is merely rotated hydraulically in order to avoid shaft distortion.

To clean the components by means of steam, the respective components, that is to say the steam lines 4.1a, 4.2, 4.3a, 4.3b, 4.4 and the temporary steam line system 4.1b and also the operational bypass lines 4.5a to 4.5c and the steam boiler device 2 with the super heater heating surfaces 2.1.3, 2.2.3, 2.3, 2.4.2 are blown out when the power plant 1 is in condensation operation. In this case, first, the high-pressure and the medium-pressure super heater 2.1.3 and 2.2.3 off the steam boiler device 2 are cleaned by setting suitable steam parameters. Steam also already flows in this cycle through the reheater 2.3 and the low-pressure super heater 2.4.2. Subsequently, by the output of a gas turbine 15 preceding the steam boiler device 2 being increased, the cleaning parameters for the reheater 2.3 and the low-pressure super heater 2.4.2 are set. The gas turbine 15 is preceded by a combustion chamber 15.1 and a compressor 15.2 for operating the gas turbine 15.

The temporary steam line system 4.1b for bypassing the high-pressure stage 6a of the steam turbine 6 is arranged between the temporary blow-out inserts 18 and is provided with a measuring device 16. By means of the measuring device 16, for example a baffle plate change device, the particles entrained in the steam are measured. The discharge of the entrained particles or foreign bodies takes place via the blow-out inserts 18 by the steam being blown out. The demineralized water afterfeed in this case takes place via a supply line 8.1 which issues into the condenser 8. The measuring device 16 is arranged in the steam lines 4.4 and 4.3b of the low-pressure stage 2.4 or of the medium-pressure stage 2.2 and in the temporary steam line system 4.1b.

In contrast to FIG. 10, a power plant 1 with a plurality of steam boiler devices 2.3 is illustrated in FIG. 11. Water or steam flows through the further steam boiler device 3 according to the feeds or discharges A to I.

The invention claimed is:

1. A method for cleaning of plant parts of a power plant, the power plant generates power during a normal operation and includes a steam medium generated in a steam boiler device, comprising:
   routing the steam medium continuously, during a condensation operation of the power plant, in a closed flow circuit, including the steam boiler device, through one or more plant parts to be cleaned wherein the closed flow circuit includes conduits that bypass a conduit path of only plant parts that are not to be cleaned and that the steam medium follows during a normal operation of the power plant; and
   testing the steam medium to determine in the closed flow circuit a degree of purity of the steam medium,
   wherein the one or more plant parts to be cleaned are cleaned by the steam medium.

2. The method as claimed in claim 1, wherein the closed flow circuit is a temporary steam line system.

3. The method as claimed in claim 1, wherein the steam medium that is extracted from the steam boiler device, and used to clean plant parts, is condensed into a liquid in a condenser that is routed in the closed flow circuit to supply the liquid to the steam boiler device to generate steam medium in the steam boiler device for cleaning the plant parts.

4. The method as claimed in claim 3, wherein a steam turbine unit provided in the power plant is bypassed by the closed flow circuit, and the steam turbine unit is not acted upon with steam during cleaning.

5. The method as claimed in claim 4, wherein a high-pressure and medium-pressure stage of a steam boiler device are cleaned in succession.

6. A system for cleaning of a plant part of a power plant, the power plant generates power during a normal operation, comprising:
   a steam boiler device;
   a steam medium generated in the steam boiler device;
   the plant part to be cleaned by the steam medium;
   a closed flow circuit, including the steam boiler device, which continuously routes the steam medium through the plant part to be cleaned and which bypasses a conduit path the steam medium follows during a normal operation of the power plant, wherein the conduit path includes only plant parts not to be cleaned; and
   a measuring device for measuring a degree of purity of the steam medium connected to the plant part to be cleaned.

7. The system as claimed in claim 6, wherein the measuring device is connected to a low-pressure steam line and/or to a medium-pressure/reheater steam line.

8. The system as claimed in claim 7, wherein the measuring device is connected to a connection piece of a temporary steam line system.

9. The system as claimed in claim 8, wherein the measuring device is opened temporarily when the power plant is in condensation operation.

10. The system as claimed in claim 9, wherein the measuring device is removed when the power plant is in the normal operation.

11. The method as claimed in claim 1, wherein the during normal operation, a generator generating electrical current is driven by a steam turbine unit.

12. The method as claimed in claim 1, wherein the during condensation operation, a steam turbine unit is rotated hydraulically.

* * * * *